(12) United States Patent
Livnat

(10) Patent No.: US 11,317,795 B2
(45) Date of Patent: May 3, 2022

(54) RESPIRATORY TUBE INSERTION METHOD

(71) Applicant: Guy Livnat, Greenbrae, CA (US)

(72) Inventor: Guy Livnat, Greenbrae, CA (US)

( * ) Notice: Subject to any disclaimer, the term of this patent is extended or adjusted under 35 U.S.C. 154(b) by 96 days.

(21) Appl. No.: 16/942,621

(22) Filed: Jul. 29, 2020

(65) Prior Publication Data

US 2020/0359883 A1   Nov. 19, 2020

Related U.S. Application Data

(63) Continuation-in-part of application No. 16/594,489, filed on Oct. 7, 2019, which is a continuation of application No. 14/149,300, filed on Jan. 7, 2014, now Pat. No. 10,433,720.

(51) Int. Cl.
| | | |
|---|---|---|
| *A61B 1/267* | (2006.01) | |
| *A61B 1/06* | (2006.01) | |
| *A61B 1/00* | (2006.01) | |
| *A61M 16/04* | (2006.01) | |

(Continued)

(52) U.S. Cl.
CPC ............ *A61B 1/267* (2013.01); *A61B 1/0014* (2013.01); *A61B 1/00052* (2013.01); *A61B 1/05* (2013.01); *A61B 1/0676* (2013.01); *A61M 16/0488* (2013.01); *A61B 1/00101* (2013.01); *A61B 1/00135* (2013.01); *A61B 5/082* (2013.01);

(Continued)

(58) Field of Classification Search
CPC .............. A61M 16/04; A61M 16/0488; A61M 16/0486; A61B 1/267; A61B 1/07; A61B 1/05; A61B 1/00016; A61B 1/06; A61B 1/0661; A61B 1/0669; A61B 1/0676; A61B 1/0692; A61B 1/04; A61B 1/042; A61B 1/0684; A61B 1/00052; A61B 1/00009; A61B 1/00032; A61B 1/00002; A61B 1/00165; A61B 1/00101; A61B 1/00135; A61B 1/0014
USPC ....... 600/188, 199, 197, 179, 194, 120, 160, 600/249, 109, 175, 173; 128/200.26
See application file for complete search history.

(56) References Cited

U.S. PATENT DOCUMENTS

| | | | | |
|---|---|---|---|---|
| 4,727,859 A | * | 3/1988 | Lia .................... | A61B 1/00101 |
| | | | | 356/241.5 |
| 5,685,822 A | * | 11/1997 | Harhen .............. | A61B 1/00142 |
| | | | | 600/121 |

(Continued)

*Primary Examiner* — Marcela I. Shirsat
(74) *Attorney, Agent, or Firm* — Mark David Torche; Patwrite Law

(57) ABSTRACT

A method using a medical apparatus includes attaching a cylindrical sleeve to a respiratory tube insertion tool, the sleeve with a distal end affixed to an outward-facing illumination device and a corresponding forward-facing imaging device, the sleeve including an open proximal end connecting a tubular cavity to an outer space, the open proximal end to slidingly receive therethrough a distal end of the insertion tool; including an inner surface around the tubular cavity configured to slide over and removably affix itself to the distal portion of the insertion tool. The method includes inserting the insertion tool with the attached sleeve into an airway of a human subject, transmitting images of the airway acquired by the imaging device to a remote device for displaying, displaying the images of the airway on the remote display device, and positioning the insertion tool with the attached sleeve inside the airway based on the images.

20 Claims, 9 Drawing Sheets

(51) Int. Cl.
*A61B 1/05* (2006.01)
*A61B 5/08* (2006.01)

(52) U.S. Cl.
CPC .... *A61B 2503/20* (2013.01); *A61M 2230/432* (2013.01)

(56) References Cited

U.S. PATENT DOCUMENTS

| | | | | |
|---|---|---|---|---|
| 7,435,218 | B2* | 10/2008 | Krattiger | A61B 1/00096 600/129 |
| 8,182,422 | B2* | 5/2012 | Bayer | A61B 1/0684 600/175 |
| 2012/0172664 | A1* | 7/2012 | Hayman | A61B 1/00045 600/109 |
| 2013/0006051 | A1* | 1/2013 | Stace | A61B 1/05 600/109 |

* cited by examiner

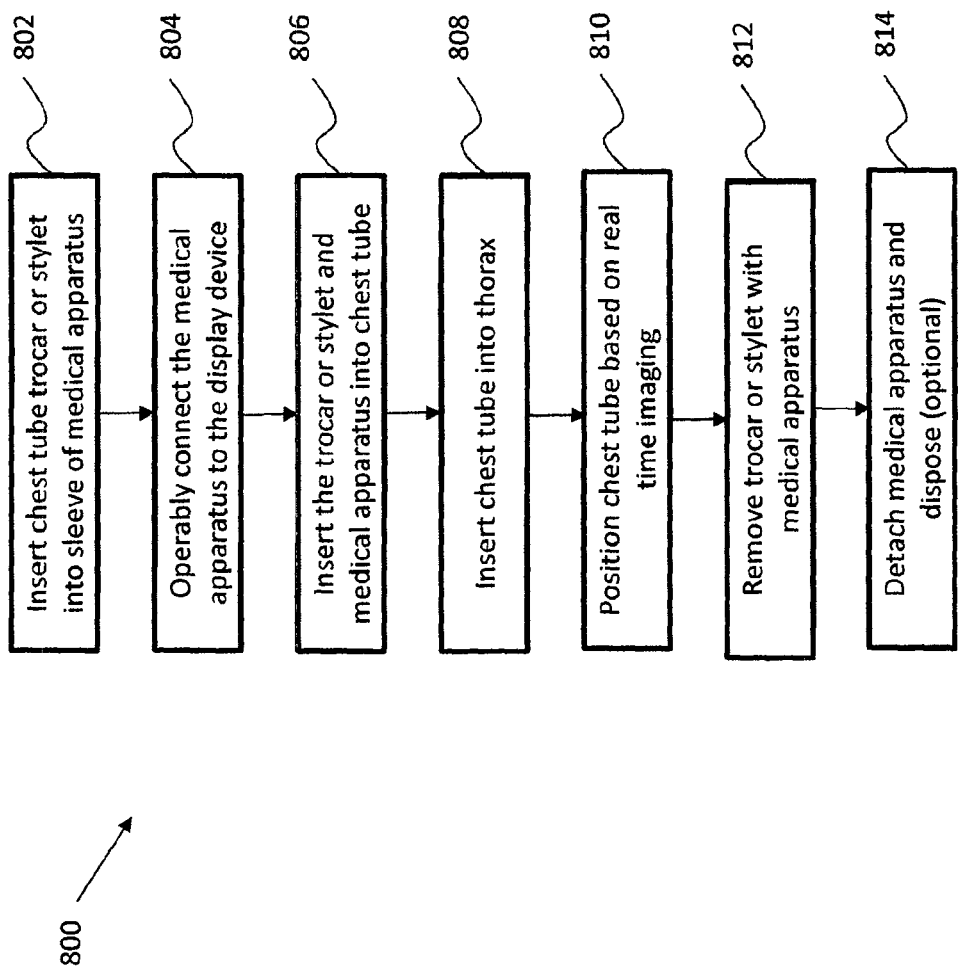

RESPIRATORY TUBE INSERTION METHOD

CROSS-REFERENCE TO RELATED APPLICATIONS

This application is a continuation-in-part application claiming benefit from U.S. patent application Ser. No. 16/594,489, filed 7 Oct. 2019, which is a continuation of U.S. patent application Ser. No. 14/149,300 filed on 7 Jan. 2014 and now U.S. Pat. No. 10,433,720, all of which are hereby incorporated in their entirety by reference.

FIELD OF THE INVENTION

The present invention relates to medical devices generally and more particularly to a method for airway management or for airway diagnostics.

BACKGROUND OF THE INVENTION

In cases where patients cannot breathe on their own or protect their own airway, proper placement and positioning of an artificial airway (for example an endotracheal tube) is critical in ensuring a patient receives adequate ventilation and oxygenation. This placement can be particularly difficult in irregular circumstances such as with local injury, unusual patient physicality and emergency situations in general. Being able to accurately visualize and identify the tracheal opening is a critical step in proper artificial airway placement. In many situations, if the artificial airway is not both accurately and quickly positioned, an undesirable outcome may occur.

There are several types of artificial airways that can be used to manage patients, each with its particular applications. Endotracheal tubes are introduced into the trachea in a procedure termed intubation utilizing dedicated intubation tools. Given the importance of accurate, timely and atraumatic placement, these tools include sophisticated, complex and expensive variations to assist in successful placement during difficult circumstances. However, due to their expense, such complex intubation devices are usually only available in limited quantities in any facility such as a hospital, and even less available in non-hospital settings such as EMT (emergency medical treatment) vehicles and medical field service facilities such as in war-zone areas.

Although intubation tools such as video laryngoscopes and video stylets are known and used, their expense limits their availability and they are not commonly a part of intubation kits. It is not uncommon, even in hospital settings that such tools are not readily available at the point of care rather such tools must be requested from another part of the hospital where stored or last in use.

Intubation tools commonly found in an intubation kit include a laryngoscope handle with sized blades; endotracheal tubes (ETT); supra-glottal artificial breathing devices such as a laryngeal mask, laryngeal tube (e.g. King LT as it is known in the U.S.); stylets; tracheal introducers; inflation syringe; and other common items such as face masks, catheters, etc.

SUMMARY OF THE PRESENT INVENTION

There is provided, in accordance with an embodiment of the present, a method for airway management or diagnostics which includes attaching a removable medical apparatus to an insertion tool suitable to be introduced into an airway, the medical apparatus including a sleeve with a distal end affixed to an outward-facing illumination device and a corresponding forward-facing imaging device. The sleeve includes an open proximal end connecting an inner cavity to an outer space, the open proximal end to slidingly receive therethrough a distal end of the insertion tool and including an inner surface around the inner cavity configured to wholly slide over and removably affix itself to the distal portion of the insertion tool. Optionally, the inner cavity comprises a tubular shape. The method additionally includes inserting the insertion tool with the attached medical apparatus into the airway of a subject, illuminating the airway with the illumination device, acquiring images of the airway with the imaging device, and transmitting images of the airway acquired by the imaging device, by means of a communication mechanism in the medical apparatus operably connected to the imaging device, to a remote device for displaying, and displaying the images of the airway on the remote display device.

In some embodiments, the method additionally includes, prior to insertion into the airway, inserting the insertion tool with the attached medical apparatus into an oro-tracheal intubation tube.

In some embodiments, the method additionally includes, prior to insertion into the airway, inserting the insertion tool with the attached medical apparatus into a nasotracheal tube.

In some embodiments, the method additionally includes, prior to insertion into the airway, inserting the insertion tool with the attached medical apparatus into a supraglottic airway device.

In some embodiments, the method additionally includes inserting the insertion tool and attached medical apparatus into a respiratory tube and positioning the imaging device at a distal end of the respiratory tube.

In some embodiments, the method additionally includes illuminating the airway with the illumination device.

In some embodiments, the method additionally includes removing the insertion tool with the attached medical apparatus from the airway.

In some embodiments, the method additionally includes detaching the medical apparatus from the insertion tool.

In some embodiments, the method additionally includes disposing of the medical apparatus.

In some embodiments, the method additionally includes sliding an endotracheal tube over the insertion tool with the attached medical apparatus.

In some embodiments, the method additionally includes positioning a respiratory tube inside the airway based on the acquired images.

In some embodiments, the respiratory tube insertion tool includes a stylet.

In some embodiments, the respiratory insertion tool includes a tracheal introducer.

In some embodiments, the transmitting includes use of wired communication means.

In some embodiments, the transmitting includes use of wireless communication means.

In some embodiments, the displayed images include real-time images.

In some embodiments, the displayed images include still-images.

In some embodiments, the method additionally includes inserting the insertion tool with the attached medical apparatus into an indwelling endotracheal tube previously inserted into the airway, positioning the imaging device at the distal end of the indwelling endotracheal tube, and adjusting a position of the indwelling endotracheal tube based on acquired images from the imaging device.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 8 is a flow diagram of an exemplary method of using the medical apparatus of FIGS. 1 and 2 for placement of a chest tube in a tube thoracostomy procedure, according to an embodiment of the present invention.

Figure 1:
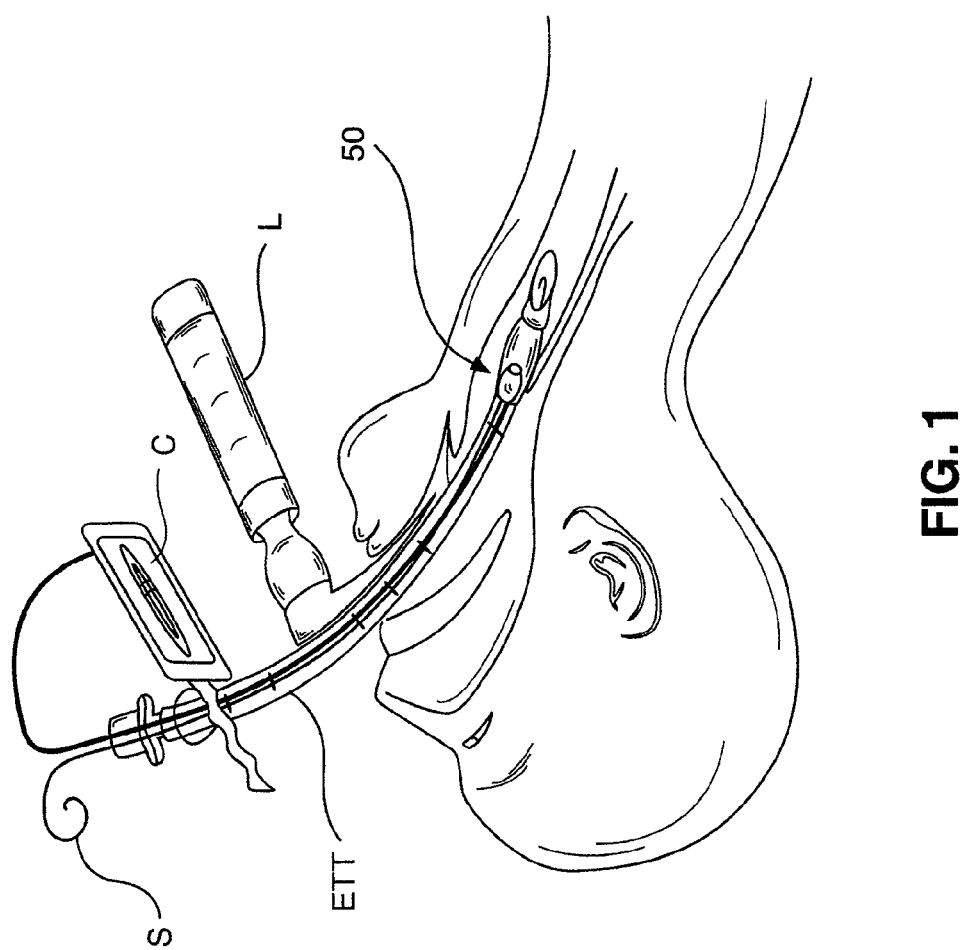
FIG. 1 schematically illustrates an embodiment of a medical apparatus in use during oro-tracheal intubation in conjunction with an intubation tube, specifically an endotracheal tube ETT, according to an embodiment of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In U.S. patent application Ser. No. 14/149,300 and now U.S. Pat. No. 10,433,720, commonly owned by the Applicant and incorporated herein by reference in its entirety, Applicant describes a medical apparatus for assisting in the insertion of a respiratory tube in a subject. The medical apparatus includes a substantially cylindrical sleeve with a distal end affixed to an outward-facing illumination device and a corresponding forward-facing imaging device. The sleeve includes an open proximal end connecting a tubular cavity to an outer space to slidingly receive therethrough a distal end of a respiratory tube insertion tool, and additionally includes an inner surface around the tubular cavity configured to wholly slide over and removably affix itself to the distal portion of the respiratory tube insertion tool.

The medical apparatus additionally includes a communication mechanism operably connected to the imaging device and configured to convey images from the imaging device for remote processing and for display on a remote display device. The forward-facing imaging device may include a video camera. The communication mechanism may include a cable for wired communications and/or may include a wireless communications system which may include use of WiFi and/or other suitable communication means (e.g. Bluetooth®). The medical apparatus may additionally include a carbon dioxide sensor to assist in the insertion of the respiratory tube.

In some embodiments, the sleeve may include at least one outwardly extending projection configured to abut an inner wall surrounding a lumen in the respiratory tube. Alternatively, the sleeve may include a threaded portion for mating with a component configured to abut the inner wall surrounding the lumen in the respiratory tube. Alternatively, the sleeve may include at least one spring configured to abut the inner wall surrounding the lumen in the respiratory tube. Alternatively, the sleeve may include a foam sleeve configured to abut the inner wall surrounding the lumen in the respiratory tube.

In some embodiments, the sleeve may be configured to affix the medical apparatus inside a lumen of an airway tube of a supra-glottic airway device. The supra-glottic device may include a laryngeal mask.

In some embodiments, the apparatus may be disposable.

Applicant has realized that the medical apparatus may have a range of medical applications other than assisting in the insertion of a respiratory tube. Aside from being used for endotracheal intubations such as oro-tracheal and nasotracheal intubations, it made also be used to perform indwelling endotracheal tube evaluations and revisions; to perform native airway diagnostics; to assist in placement of supra-glottic airway devices; and to assist in placement of a surgical chest tube in a tube thoracostomy procedure; among other possible applications.

Figure 2:
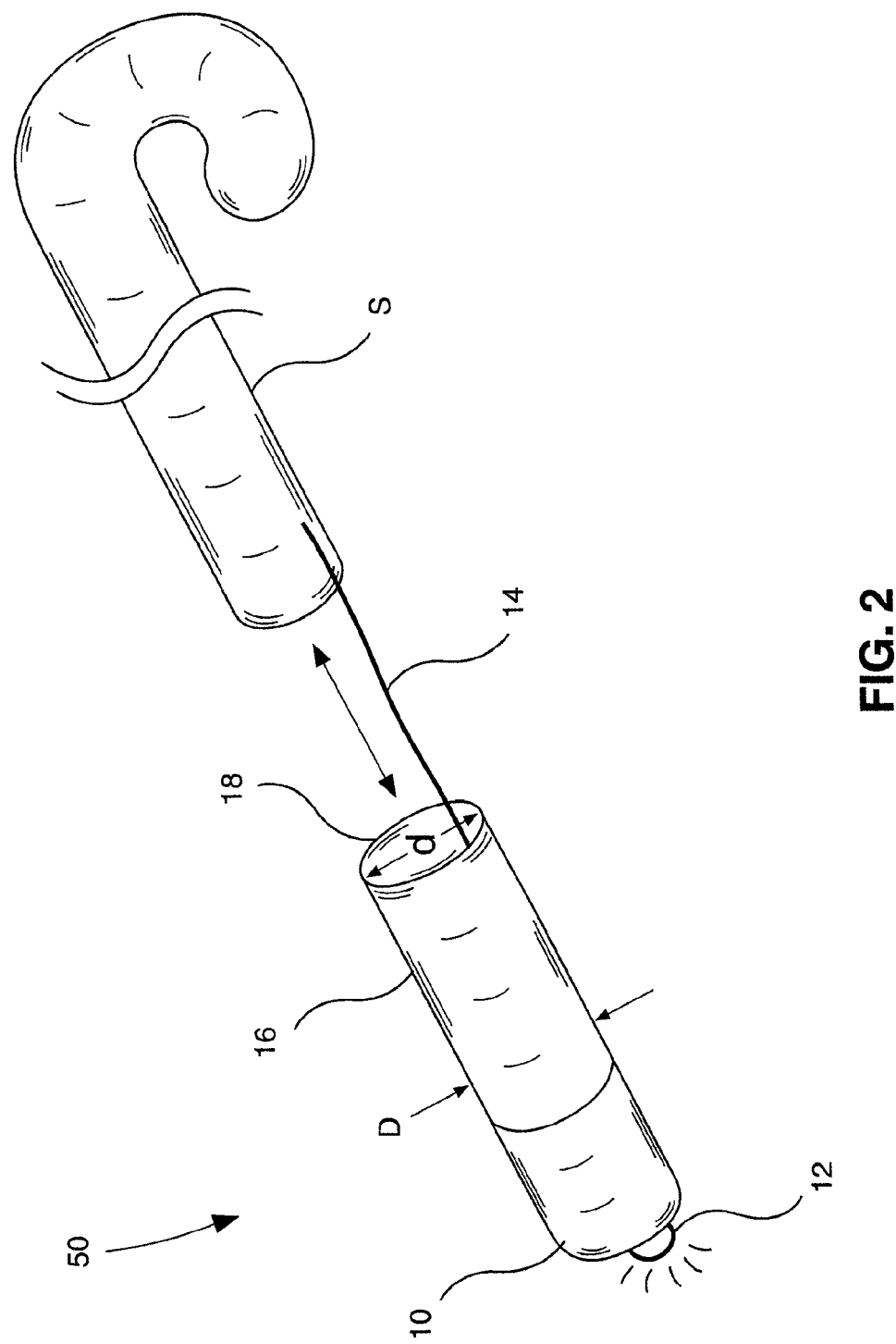
FIG. 2 schematically illustrates a detailed view of the medical apparatus of FIG. 1, according to an embodiment of the present invention.

The medical apparatus of the present invention is shown in FIGS. 1 and 2 and, for exemplary purposes, is mainly described therein in conjunction with an endotracheal tube. Nevertheless, the skilled person will appreciate that the medical apparatus may be used in other medical applications, as previously mentioned and described by the Applicant in greater detail further on below.

FIG. 1 shows an embodiment of the medical apparatus 50 in use during oro-tracheal intubation in conjunction with an intubation tube, specifically an endotracheal tube ETT, according to an embodiment of the present invention. For such intubation procedures, laryngoscopy is commonly performed with a laryngoscope L first placed in a patient's upper airway to mobilize the tongue to assist in exposing the tracheal opening. Endotracheal tube ETT is then inserted into the patient's airway and placed so as to provide air/oxygen to the patient, with the aid of a display screen C that is operably attached to the medical apparatus.

Entry to the patient's airway and proper placement is often facilitated by a malleable stylet S, to pre-form the inherently flexible endotracheal tube ETT to a desired shape for the procedure, as illustrated, or a tracheal introducer, which is a flexible rod, typically made of plastic having a profile or cross-section similar to a stylet with an optional coude tip that is used to intubate the trachea and serve as a guide over which the ETT is then introduced into position. Stylet S can be additionally utilized either as a mount for medical apparatus 50 within the endotracheal tube or to position the medical apparatus at the distal end of the ETT itself for optimal visualization. Following successful intubation, stylet S (or the tracheal introducer) is then removed, along with medical apparatus 50, or, the medical apparatus is removed shortly thereafter.

FIG. 2 shows a detailed view of medical apparatus 50, according to an embodiment of the present invention. Medical apparatus 50 includes an image capturing device 10 (e.g. video camera), typically having an illumination member 12 associated therewith or integral thereto; a communication mechanism 14, such as a cable, as illustrated, or a wireless system, operably connected to the image capturing device for communicating images from the image capturing device to a display screen, such as display screen C, to facilitate visualizing the patient's airway; and a sleeve 16 configured for interfacing (i.e. removably fixing) medical apparatus 50 with the intubation tool (e.g. endotracheal tube ETT) or to appropriate positioning devices such as stylet S, introducer N, or the like. Illumination member 12 can be configured as a combination of an illumination source and image capturing/camera lens.

Image capturing device 10 (including illumination member 12 where applicable) and communication mechanism 14 can be collectively considered as components of a data acquisition unit of medical apparatus 50. In some embodiments, a fiber optic tube, or the like, is configured to be attachable to an intubation tool and communicates with imaging capture device 10, which can thereby be positioned external of the patient.

In this embodiment, sleeve 16 has a generally cylindrical shape defining a tubular cavity 18 configured to receive the distal end of stylet S in order to place medical apparatus 50 onto the end of the stylet (or the tracheal introducer), for example. In some embodiments, sleeve 16 is made of a relatively soft or flexible plastic, or the like, thereby providing some flexible quality to help provide ease and range of fit.

It should be understood that sleeve 16 of medical apparatus 50 may have a range of sizes to thereby suit ETT's and other artificial airways such as super-glottic airways as well as intubation tools/positioning devices such as stylet S and the tracheal introducer of different sizes. In this regard, it should be understood that (a) the outer diameter "D" of sleeve 16 may be dimensioned to facilitate a somewhat snug fit within the ETT, while being reasonably easily removable therefrom; and/or (b) the inner diameter "d" of cavity 18 may be dimensioned to facilitate a similar fit over stylet S or the tracheal introducer. After placement of the ETT, medical apparatus 50 is removed, just as a video stylet or video introducer would be removed.

FIGS. 3A and 3B through 8 below show flowcharts of exemplary methods of using the medical apparatus of the present invention. It may be appreciated that use of the medical apparatus of the present invention is particularly advantageous over existing devices due to its ease of use, its manufacturing simplicity, and its low cost, all of which may make it readily disposable following use. Accordingly, the flow charts and associated description each include a final step which is optional and includes disposing of the medical apparatus.

It may be appreciated by the skilled person that the exemplary methods described below may be practiced using more steps or less steps, and/or using a different sequence of steps. It may be further appreciated by the skilled person that real time imaging and still image documentation may be acquired using the medical apparatus during one or more steps of each procedure and that the acquired images may be displayed to the physician or other medical personnel, hereinafter the "user", in real time during the one or more steps using a display device (e.g display device C).

In describing the flowcharts shown in FIGS. 3A and 3B through 8, reference may be made to medical apparatus 50 shown in FIGS. 1 and 2, and to other components shown therein, to assist in the understanding of the description. It is noted that throughout the description of the flowcharts shown in the figures, reference may be made to stylet S or to a tracheal introducer as an example of a suitable insertion tool. Nevertheless, the ordinary person skilled in the art may appreciate that a suitable insertion tool may not be limited to a "stylet" or a "tracheal introducer", rather to any suitable instrument to which the medical apparatus may be removably attached and which may be introduced into a subject's airway, or may be introduced into a respiratory tube and/or assist in the introduction of a respiratory tube into the airway of the subject.

In describing the flowcharts shown in FIGS. 3A and 3B, 4, 7 and 8, the steps may include inserting the insertion tool together with the attached medical apparatus into the naso-ETT or the oro-ETT or the supra-glottic device or the chest tube (i.e., respiratory tubes) and removing the insertion tool together with the medical apparatus following proper placement of the respiratory tubes. It is noted that, in some embodiments, the insertion tool with the attached medical apparatus may be inserted into the respiratory tube followed by the subsequent extraction of the insertion tool while leaving the medical apparatus inside the respiratory tube. Following extraction of the insertion tool, the respiratory tube may be guided into the subject's airway by the user, guided by images acquired by the medical apparatus. The medical apparatus may be removed following insertion of the respiratory tube.

Endotracheal Intubation

Endotracheal intubation generally involves the placement of a flexible plastic tube into the trachea to maintain an open airway or to serve as a conduit through which to administer certain drugs. It is frequently performed in critically injured, ill, or anesthetized patients to facilitate ventilation of the lungs, including mechanical ventilation, and to prevent the possibility of asphyxiation or airway obstruction. A common technique for endotracheal intubation is the oro-tracheal procedure in which the endotracheal tube is passed through the mouth and vocal apparatus into the trachea. Another technique is the nasotracheal procedure where the endotracheal tube is passed through the nose and vocal apparatus into the trachea.

Figure 3A:
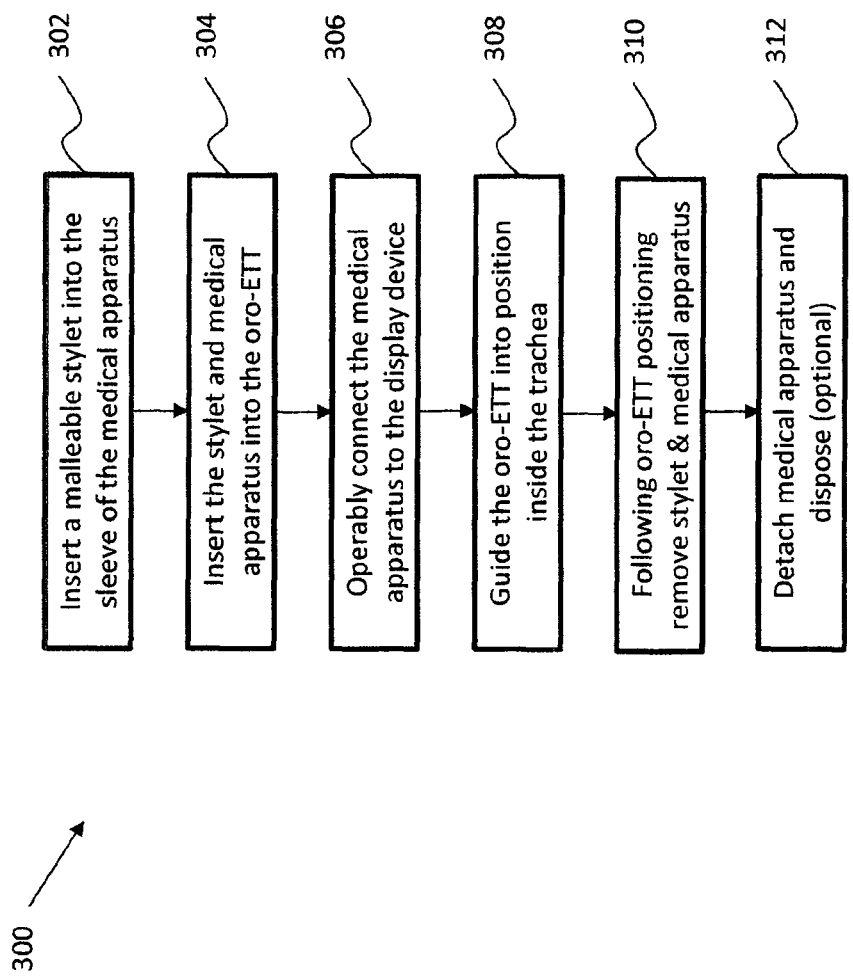
FIG. 3A is a flow diagram of an exemplary method of using the medical apparatus of FIGS. 1 and 2 to perform an oro-tracheal intubation procedure, according to an embodiment of the present invention.

Oro-tracheal Intubation:
Oro-tracheal Intubation:
Oro-tracheal Intubation:

FIG. 3A is a flow diagram of an exemplary method 300 of using medical apparatus 50 to perform an oro-tracheal intubation procedure, according to an embodiment of the present invention.

At 302, a user may insert a distal end of a suitable insertion tool, for example a malleable stylet S, into sleeve 16 in medical apparatus 50 to attach the medical apparatus to the stylet.

At 304, the user may insert stylet S with attached medical apparatus 50 into an oro-tracheal tube (oro-ETT) until the medical apparatus is positioned proximal to the distal opening of oro-ETT.

At 306, the user operably connects medical apparatus 50 by means of wireless and/or wired communications to allow displaying by device C real time video acquired by imaging capturing device 10.

At 308, the user may guide, based on the displayed real time imaging in display C, the oro-ETT to the desired location inside the trachea.

At 310, following positioning of the oro-ETT at the desired location, the user may extract stylet S with attached medical apparatus from inside the oro-ETT, leaving the oro-ETT in place within the trachea.

At 312, the user optionally detaches medical apparatus 50 from stylet S and disposes of the medical apparatus.

Figure 3B:
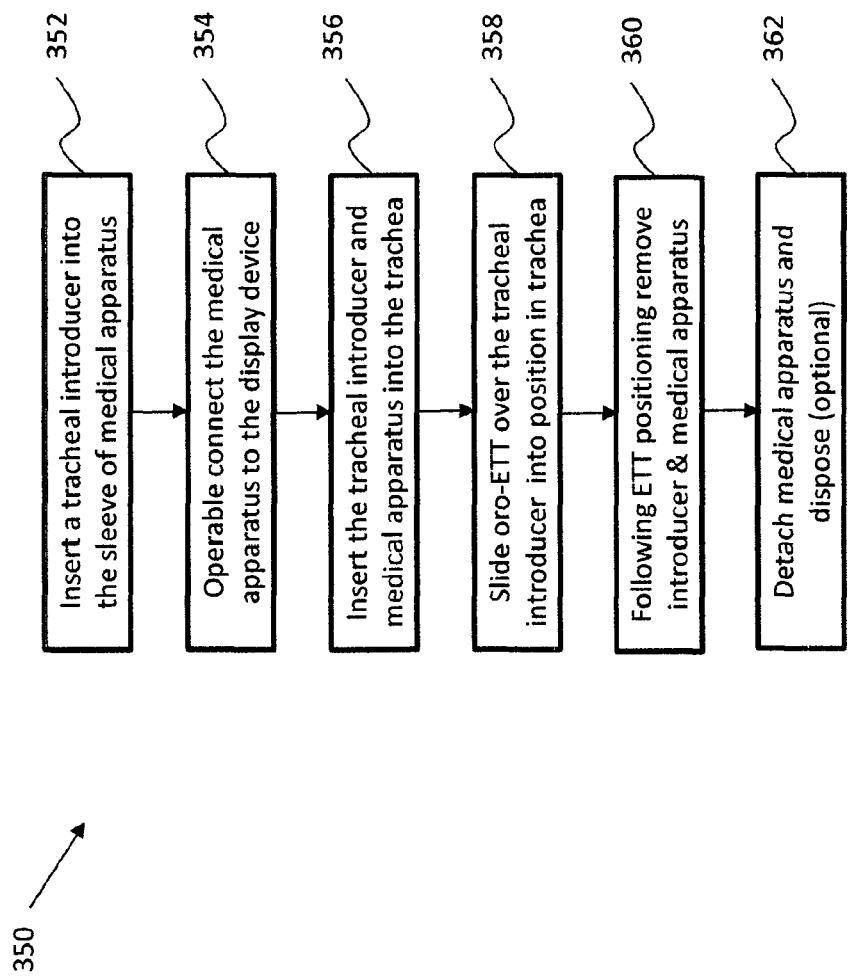
FIG. 3B is a flow diagram of another exemplary method of using the medical apparatus of FIGS. 1 and 2 to perform an oro-tracheal intubation procedure, according to an embodiment of the present invention.

FIG. 3B is a flow diagram of another exemplary method 350 of using medical apparatus 50 to perform an oro-tracheal intubation procedure, according to an embodiment of the present invention.

At 352, a user may insert a distal end of a suitable insertion tool, for example a tracheal introducer, into sleeve 16 in medical apparatus 50 to attach the medical apparatus to the tracheal introducer.

At 354, the user operably connects medical apparatus 50 by means of wireless and/or wired communications to allow displaying by device C real time video acquired by imaging capturing device 10.

At 356, the user may insert the tracheal introducer with attached medical apparatus 50 into the patient's trachea, based on the displayed real time imaging in display C, to a desired location inside the trachea.

At 358, the user may slide the oro-ETT over the tracheal introducer into the patient's trachea and, using imaging from medical apparatus 50, to position inside the trachea.

At 360, following positioning of the oro-ETT at the desired location, the user may extract the tracheal introducer with attached medical apparatus 50 from inside the oro-ETT, leaving the oro-ETT in place within the trachea.

At 362, the user optionally detaches medical apparatus 50 from the tracheal introducer and disposes of the medical apparatus.

Figure 4:
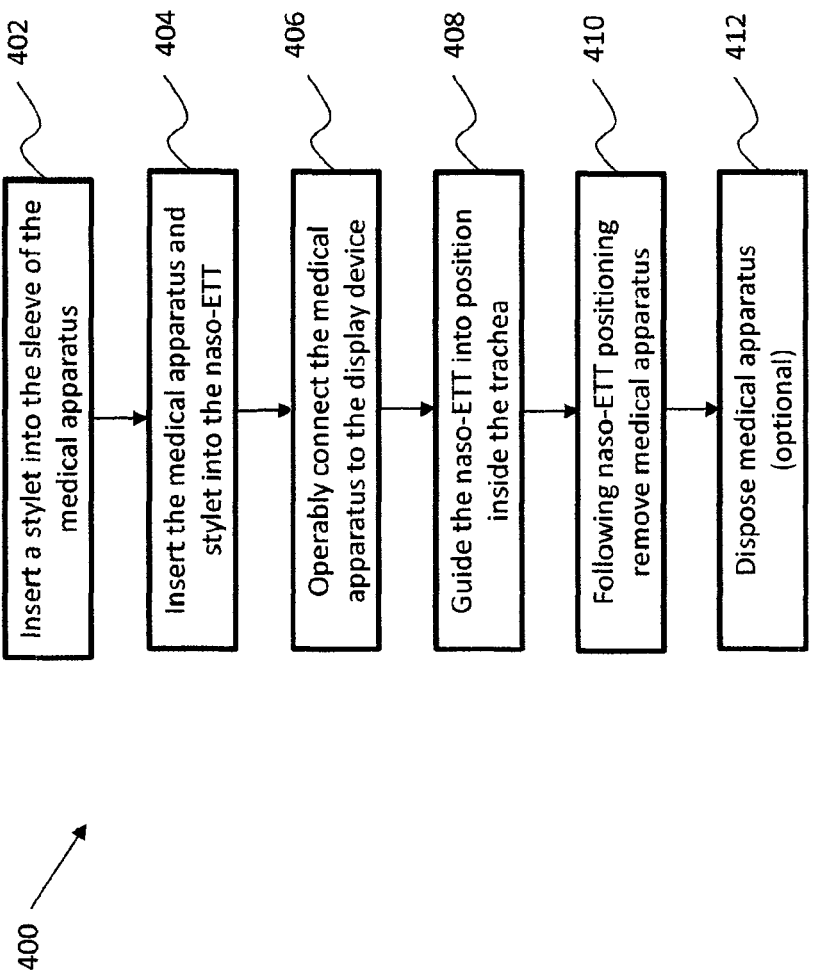
FIG. 4 is a flow diagram of an exemplary method of using the medical apparatus of FIGS. 1 and 2 to perform a nasotracheal intubation procedure, according to an embodiment of the present invention.

Nasotracheal Intubation:

FIG. 4 is a flow diagram of an exemplary method 400 of using medical apparatus 50 to perform a nasotracheal intubation procedure, according to an embodiment of the present invention.

At 402, a user may insert a distal end of a suitable insertion tool, for example, a thin malleable stylet S, into sleeve 16 in medical apparatus 50 to attach the medical apparatus to the stylet.

At 404, the user may insert stylet S with attached medical apparatus 50 into naso-ETT until the medical apparatus is positioned proximal to the distal opening of naso-ETT.

At 406, the user operably connects medical apparatus 50 by means of wireless and/or wired communications to allow displaying by device C real time video acquired by imaging capturing device 10.

At 408, the user may guide, based on the displayed real time imaging in display C, the nasotracheal tube (naso-ETT) to the desired location inside the trachea.

At 410, following positioning of naso-ETT at the desired location, the user may extract stylet S with attached medical apparatus from inside the naso-ETT, leaving naso-ETT in place within the trachea.

At 412, the user optionally disposes of medical apparatus 50.

Indwelling Endotracheal Tube Evaluation

Patients are sometimes confined to long periods of times with a tracheal intubation. Frequently, the tracheal tubes are connected to a mechanical ventilating tube which in turn is connected to a source of flowing air or oxygen. These tracheal tubes, generally known as indwelling endotracheal tubes, once placed and over time, may change their position which may cause complications which may interfere with the patient's ventilation. Furthermore, complications may arise which may not necessarily be caused by the tube's movement. Consequently, periodic review of the ETT's condition, patency and position is required.

Figure 5:
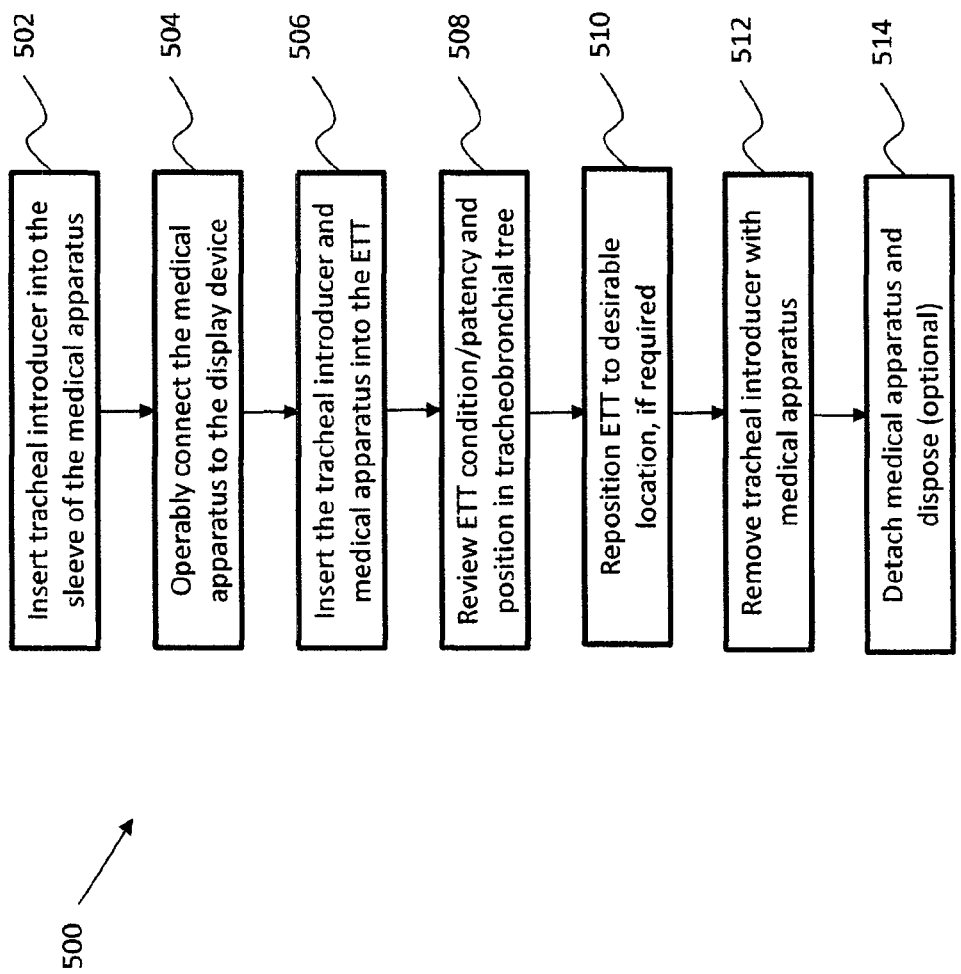
FIG. 5 is a flow diagram of an exemplary method of using the medical apparatus of FIGS. 1 and 2 to perform an indwelling endotracheal tube evaluation and revision, according to an embodiment of the present invention.

FIG. 5 is a flow diagram of an exemplary method 500 of using medical apparatus 50 to perform an indwelling endotracheal tube evaluation and revision, according to an embodiment of the present invention.

At 502, a user may insert a distal end of a suitable insertion tool, for example a tracheal introducer, into sleeve 16 in medical apparatus 50 to attach the medical apparatus to the introducer.

At 504, the user operably connects medical apparatus 50 by means of wireless and/or wired communications to allow displaying by device C real time video acquired by imaging capturing device 10.

At 506, the user may insert the tracheal introducer with attached medical apparatus 50 into the indwelling ETT using an appropriate adaptor.

At 508, the user may review the condition of the ETT including patency and its position in the tracheobronchial tree based on the displayed real time imaging in display C.

At 510, the user may reposition the ETT, if required, based on the displayed real time imaging in display C, to the desired location inside the trachea.

At 512, following repositioning of ETT at the desired location, the user may extract the tracheal introducer with attached medical apparatus 50 from inside the ETT, leaving ETT in place within the trachea. The adaptor may also be removed.

At 514, the user optionally detaches medical apparatus 50 from the tracheal introducer and disposes of the medical apparatus.

Native Airway Diagnostics

Evaluation of a person's native airway may be performed to assess any possible degree of blocking in the person's airway and to evaluate any conditions which may interfere with gas flow. It may also be used to evaluate the conditions of a person's vocal cords, among other airway conditions.

Figure 6:
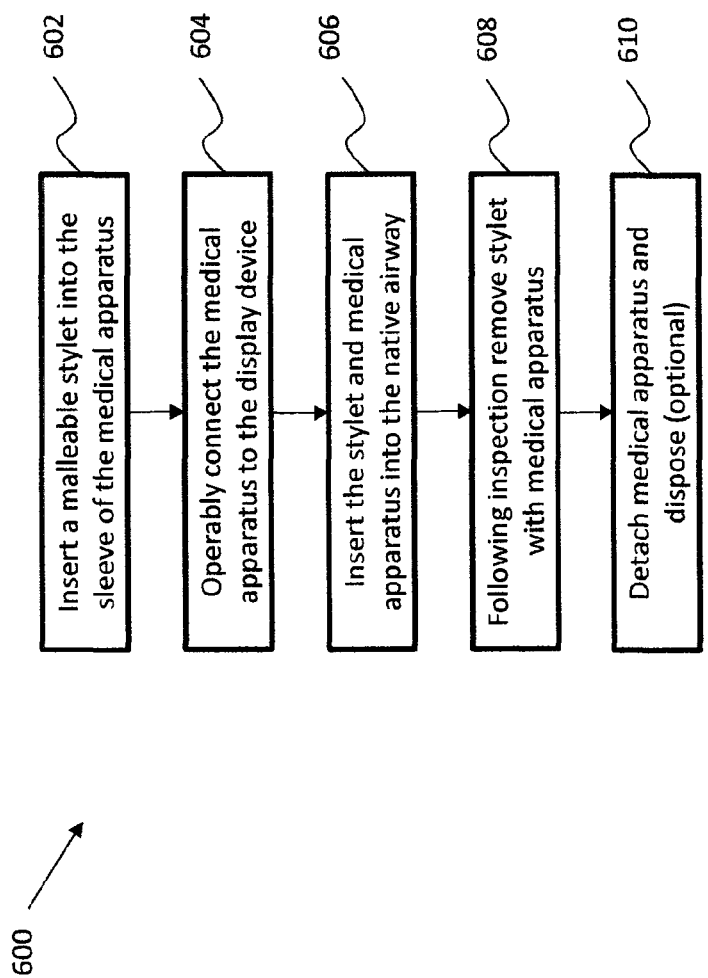
FIG. 6 is a flow diagram of an exemplary method of using the medical apparatus of FIGS. 1 and 2 to perform a native airway evaluation, according to an embodiment of the present invention.

FIG. 6 is a flow diagram of an exemplary method 600 of using medical apparatus 50 to perform a native airway evaluation, according to an embodiment of the present invention.

At 602, a user may insert a distal end of suitable insertion tool, for example malleable stylet S, into sleeve 16 in medical apparatus 50 to attach the medical apparatus to the stylet.

At 604, the user operably connects medical apparatus 50 by means of wireless and/or wired communications to allow displaying by device C real time video acquired by imaging capturing device 10.

At 606, the user may insert, based on the displayed real time imaging in display C, the stylet S with attached medical apparatus 50 into a patient's throat to inspect the airway.

At 608, following inspection of the airway, the user may extract stylet S with attached medical apparatus 50 from inside the throat.

At 610, user optionally disposes of medical apparatus 50.

Supraglottic Airway Device (SAD) Placement

Supraglottic airway devices (SADs) are generally designed to have the distal tip resting above the level of the glottis when in its final placement position. SADs may ensure patency of the upper respiratory tract without entry into the trachea. The most commonly used devices include laryngeal masks and supraglottic tubes.

Figure 7:
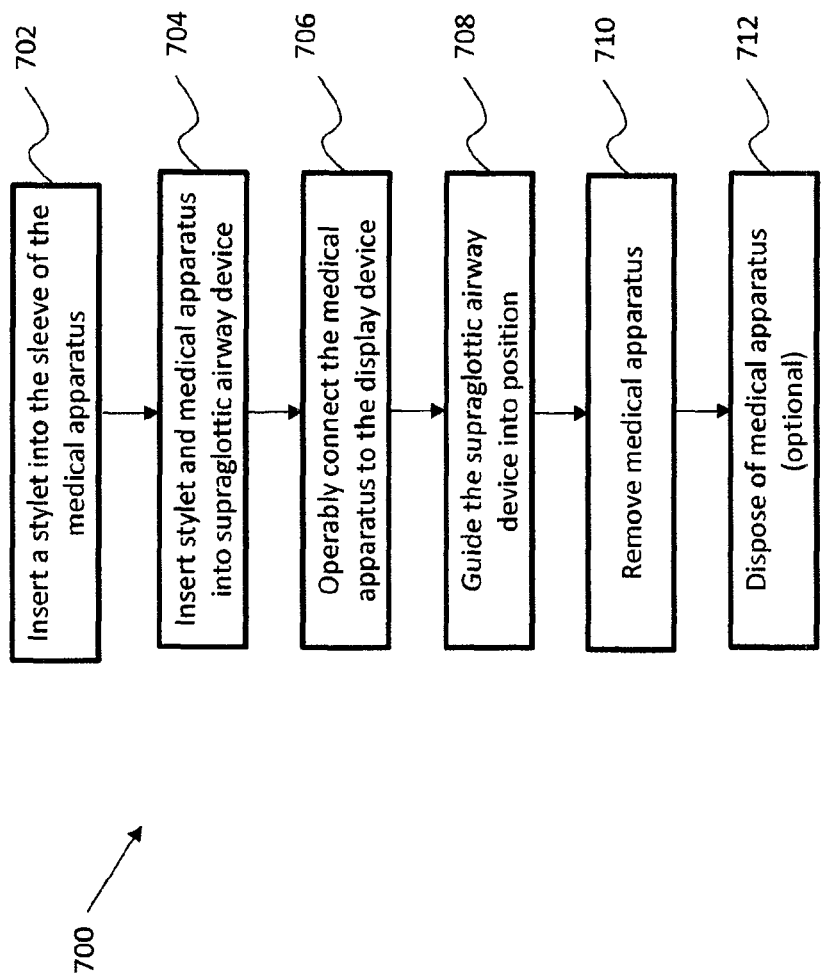
FIG. 7 is a flow diagram of an exemplary method of using the medical apparatus of FIGS. 1 and 2 for placement of a supraglottic airway device, according to an embodiment of the present invention.

FIG. 7 is a flow diagram of an exemplary method 700 of using medical apparatus 50 for placement of a supraglottic airway device, according to an embodiment of the present invention.

At 702, a user may insert a distal end of a suitable insertion tool, for example, malleable stylet S, into sleeve 16 in medical apparatus 50 to attach the medical apparatus to the stylet.

At 704, the user may insert stylet S with attached medical apparatus 50 into the SAD until the medical apparatus is positioned proximal to the distal opening of the SAD.

At 706, the user operably connects medical apparatus 50 by means of wireless and/or wired communications to allow displaying by device C real time video acquired by imaging capturing device 10.

At 708, the user may guide, based on the displayed real time imaging in display C, the SAD to the desired position.

At 710, following positioning of the SAD at the desired position, the user may extract medical apparatus 50 from inside the SAD.

At 712, the user optionally disposes of medical apparatus 50.

Tube Thoracostomy Placement

A chest tube (tube thoracostomy) is a flexible plastic tube that is inserted through the chest wall and into the pleural space or mediastinum. It is used to remove air and/or fluid from the intrathoracic space. A small incision is generally made in the skin and a passage made through the skin and muscle into the chest through which the chest tube is inserted.

FIG. 8 is a flow diagram of an exemplary method 800 of using medical apparatus 50 for placement of a chest tube in a tube thoracostomy procedure, according to an embodiment of the present invention.

At 802, a user may insert a distal end of a suitable insertion tool, for example a chest tube trocar or stylet S, into sleeve 16 in medical apparatus 50 to attach the medical apparatus to the trocar or stylet.

At 804, the user operably connects medical apparatus 50 by means of wireless and/or wired communications to allow displaying by device C real time video acquired by imaging capturing device 10.

At 806, the user may insert the trocar or stylet S with attached medical apparatus 50 into the into a chest tube.

At 808, the user may insert the chest tube with the trocar or stylet S and attached medical apparatus 50 into a patient's thorax.

At 810, the user may position the chest tube, based on the displayed real time imaging in display C, to the desired location inside the thorax.

At 812, following positioning of the chest tube at the desired location in the thorax, the user may extract the trocar or stylet S with attached medical apparatus 50 from inside the chest tube, leaving the chest tube in place within the thorax.

At 814, the user optionally detaches medical apparatus 50 from the trocar or stylet S and disposes of the medical apparatus.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method for airway management or diagnostics comprising:

attaching a removable medical apparatus to an insertion tool suitable to be introduced into an airway, the apparatus comprising a sleeve with a distal end affixed to an outward-facing illumination device and a corresponding forward-facing imaging device, said sleeve comprising an open proximal end connecting an inner cavity to an outer space, said open proximal end to slidingly receive therethrough a distal end of said insertion tool, and including an inner surface around said inner cavity configured to wholly slide over and removably affix itself to the distal portion of said insertion tool, the apparatus further comprising a communication mechanism operably connected to said imaging device and configured to transmit images from said imaging device to a display device;

inserting the insertion tool with said attached medical apparatus into the airway of a subject;

illuminating the airway with said illumination device;

acquiring images of the airway with said imaging device;

transmitting said images to a remote device for displaying; and displaying said images of the airway on said remote display device.

2. A method according to claim 1 further comprising, prior to insertion into the airway, inserting said insertion tool with said attached medical apparatus into an oro-tracheal intubation tube.

3. A method according to claim 1 further comprising, prior to insertion into the airway, inserting said insertion tool with said attached medical apparatus into a nasotracheal intubation tube.

4. A method according to claim 1 further comprising, prior to insertion into the airway, inserting said insertion tool with said attached medical apparatus into a supraglottic airway device.

5. A method according to claim 1 comprising inserting said insertion tool and attached medical apparatus into a respiratory tube and positioning said imaging device at a distal end of the respiratory tube.

6. A method according to claim 1 further comprising illuminating the airway with the illumination device.

7. A method according to claim 1 further comprising removing said insertion tool with said attached medical apparatus from the airway.

8. A method according to claim 1 further comprising detaching said medical apparatus from said insertion tool.

9. A method according to claim 1 further comprising disposing of said medical apparatus.

10. A method according to claim 1 further comprising sliding an endotracheal tube over the insertion tool with said attached medical apparatus.

11. A method according to claim 1 further comprising positioning a respiratory tube inside the airway based on said acquired images.

12. A method according to claim 1 wherein said insertion tool comprises a stylet.

13. A method according to claim 1 wherein said insertion tool comprises a tracheal introducer.

14. A method according to claim 1 wherein said transmitting comprises use of wired communication means.

15. A method according to claim 1 wherein said transmitting comprises use of wireless communication means.

16. A method according to claim 1 wherein said displayed images comprise real-time images.

17. A method according to claim 1 wherein said displayed images comprise still-images.

18. A method according to claim 1 further comprising inserting said insertion tool with said attached medical apparatus into an indwelling endotracheal tube previously inserted into the airway.

19. A method according to claim 18 comprising positioning said imaging device at a distal end of said indwelling endotracheal tube.

20. A method according to claim 18 comprising adjusting a position of said indwelling endotracheal tube based on acquired images from said imaging device.

* * * * *